US00PP13523P2

(12) United States Plant Patent
Lemon

(10) Patent No.: US PP13,523 P2
(45) Date of Patent: Jan. 28, 2003

(54) GERANIUM PLANT NAMED 'STARDOM RED'

(75) Inventor: David Lemon, County of Santa Barbara, CA (US)

(73) Assignee: Oglevee, Ltd., Connellsville, PA (US)

( * ) Notice: Subject to any disclaimer, the term of this patent is extended or adjusted under 35 U.S.C. 154(b) by 0 days.

(21) Appl. No.: 09/877,163

(22) Filed: Jun. 8, 2001

(51) Int. Cl.[7] ..... A01H 5/00
(52) U.S. Cl. ..... Plt./329
(58) Field of Search ..... Plt./329

*Primary Examiner*—Bruce R. Campell
*Assistant Examiner*—Annette Para
(74) *Attorney, Agent, or Firm*—Webb Ziesenheim Logsdon Orkin & Hanson, P.C.

(57) ABSTRACT

A new and distinct zonal geranium plant orange-red colored flowers above medium green foliage.

1 Drawing Sheet

CLASSIFICATION

*Pelargonium×hortorum* (zonal geranium).

VARIETAL DENOMINATION

'Stardom Red'.

BACKGROUND OF THE INVENTION

The present invention comprises a new and distinct cultivar of *Pelargonium×hortorum* known by the varietal name 'Stardom Red', Breeder No. 6DG2548. The new variety was discovered in Lompoc, Calif. The new variety is a result of cross breeding of Floribunda Red Seedling #1321 (female) (unpatented) and Deacon Fireball (male) (unpatented). The new variety exhibits similar flower color to both parents, but has improved flower type and flower form, and is more free flowering than its parents. The flowers of the new variety have deeper color and improved form over 'Elizabeth' (U.S. Plant Pat. No. 8,192). The new variety was first asexually reproduced by cuttings in Connellsville, Pa. The new variety has been trial and field tested and has been found to retain its distinctive characteristics and remain true to type through successive propagations.

The new variety, when grown in a glass greenhouse in Connellsville, Pa. using full light, 60° F. night temperature and 68° F. day temperature and grown in a soilless media with constant fertilizer at 200–250 ppm nitrogen and potassium has a response time of six weeks to flowering from a rooted cutting to flowering in a 10 cm pot.

DESCRIPTION OF THE DRAWING

The accompanying photographic drawing illustrates the new variety, with the color being as nearly true as is possible with color illustrations of this type.

DESCRIPTION OF THE PLANT

The following detailed description sets forth the characteristics of the new variety at 12 weeks grown from a rooted cutting. The data which define these characteristics were collected from asexual reproductions carried out at Oglevee, Ltd., 152 Oglevee Lane, Connellsville, Pa. 15425. The color readings on a plant in a 4 inch pot were taken on May 8, 2000 indoors under 200–220 foot candles of cool white fluorescent light. Color references are primarily to The R.H.S. Colour Chart of The Royal Horticultural Society of London.

PLANT

Form: Uniform mound.
Height from media surface: 15–19 cm.
Foliage: Stalked leaf attachment.
Rooting time: 14–21 days to visible root.
Leaves:
- *Size.*—7.5–9.0 cm long; 8.3–10.5 cm wide.
- *Shape.*—Reniform; cordate base.
- *Margin.*—Crenate.
- *Texture.*—Pubescent.
- *Color.*—Upper surface: Green Group 137A with zone of Greyed-Purple Group 187A. Lower surface: Green Group 137C.
- *Ribs and veins.*—Type: Palmate. Color: Yellow-Green Group 144D.

Petioles:
- *Color.*—Yellow-Green Group 144A.
- *Length.*—6.0–10 cm.

Stem:
- *Color.*—Yellow-Green Group 144A.
- *Internode length.*—2.5–4.0 cm.

THE BUD

Shape when just showing color:
- *Overall.*—Semi-spherical.
- *Individual bud.*—Round.

Size when just showing color:
- *Size of cluster.*—2.5–2.7 cm wide.
- *Individual bud.*—0.5 cm wide; 0.5 cm long.
- *Number of buds per cluster.*—11–15.

INFLORESCENCE

Blooming habit: Continuous flowering.
Size of umbel: 9–12 cm wide.
Borne: Flowers on pedicel; pedicel on peduncle; 8–12 cm above foliage.
Flowers per umbel: 20–30.
Flowers:
- *Form.*—Extremely ruffled, petals overlap, slightly cupped.

*Size.*—4.0–4.5 cm wide; 1.0–2.5 cm long.

*Petals.*—Shape: Round at outer edge with a narrower base. Size: 1.3–2.0 cm wide; 2.0–2.6 cm deep. Margin: Complete. Number per flower: 13–15. Color: Upper surface: Red Group 44A, some with small streaks of Red Group 45A. Petals have white base; some have darker veining of Red Group 46A. Lower surface: Red Groups 44B and 44C; some petals fade to a Red Group 44D at base. All petals are white at very base. Some petals have darker veining of Red Group 46B.

*Texture.*—Smooth, highly reflective.

*Tonality at a distance.*—Bright red-orange ruffled flowers highly reflective giving each petal tremendous depth.

Petaloids:

*Quantity.*—0–8.

*Shape.*—Irregular; some petal-like, some with cut edges, some tubular, some long and thin, some anther-like holding pollen.

*Color.*—Same as petals.

Pedicel:

*Length.*—3.2–3.5 cm.

*Color.*—Greyed-Purple Group 187B.

Peduncle:

*Length.*—10.5–21 cm.

*Color.*—Yellow-Green Group 144A.

Disease/pest resistance: No unusual susceptibility to diseases or pests has been noted to date.

Lasting quality: 7–14 days for each umbel.

Fragrance: None.

REPRODUCTIVE ORGANS

Stamens:

*Quantity.*—1–5 often attached to petaloids.

*Anthers.*—0.2 cm long.

*Filaments.*—Length: 0.5–0.6 cm. Color: White with peachy-red tips.

*Pollen color.*—Orange.

Pistils:

*Number.*—One.

*Length.*—0.7–0.9 cm.

*Stigma.*—Number: One. Color: Dark red-burgundy.

*Style.*—Length: 0.3–0.5 cm. Color: Dark red-burgundy.

Ovaries:

*Color.*—Green.

*Length.*—0.5 cm.

*Width.*—0.2 cm.

*Pubescence.*—Yes.

*Completeness.*—Superior.

Fruit: None observed.

I claim:

1. A new and distinct variety of zonal geranium plant substantially as shown and described.

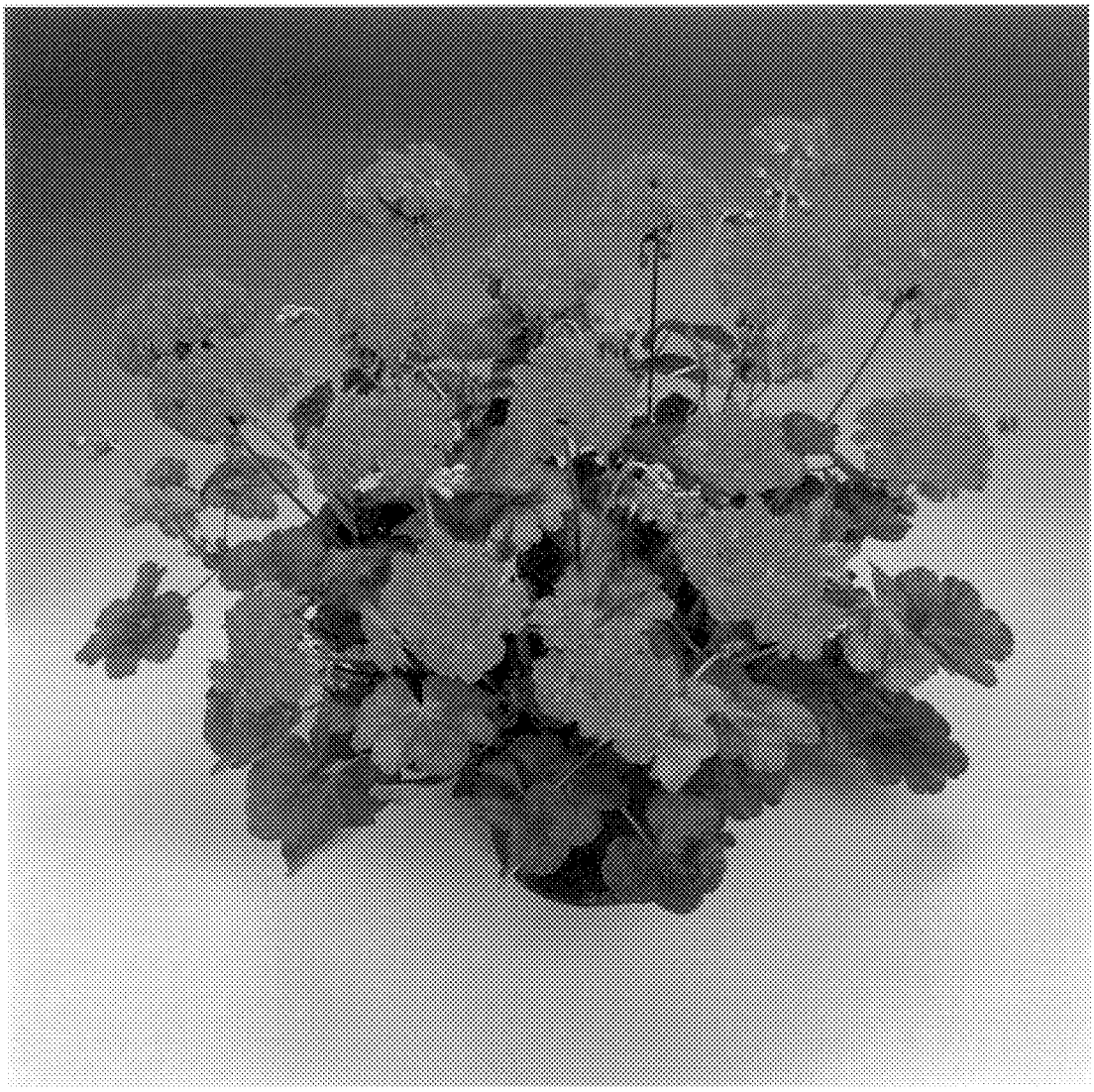

* * * * *